United States Patent [19]

Booher

[11] 3,962,269

[45] June 8, 1976

[54] 1,3-PROPANDIOL INTERMEDIATES

[75] Inventor: Richard N. Booher, Indianapolis, Ind.

[73] Assignee: Eli Lilly and Company, Indianapolis, Ind.

[22] Filed: May 8, 1975

[21] Appl. No.: 575,561

Related U.S. Application Data

[60] Division of Ser. No. 427,944, Dec. 26, 1973, which is a continuation-in-part of Ser. No. 313,221, Dec. 8, 1972, abandoned.

[52] U.S. Cl. .................... 260/296 R; 260/239 E; 260/293.67; 260/293.69; 260/293.84; 260/326.5 R; 260/326.5 D; 260/340.7; 260/570.5 R; 424/263; 424/267; 424/274; 424/278

[51] Int. Cl.² ..................................... C07D 213/38

[58] Field of Search ...... 260/239 E, 293.69, 293.84, 260/296 R, 326.5 R, 570.5 R

[56] References Cited

OTHER PUBLICATIONS

Blicke et al., J. Amer. Chem. Soc. 76, 1226–1229 (1954).
Cheymol et al., Compt. rend. 250, 1498–1500 (1961).
Schipper et al., J. Org. Chem. 26, 4145–4148 (1961).

*Primary Examiner*—G. Thomas Todd
*Attorney, Agent, or Firm*—William B. Scanlon; Everet F. Smith

[57] ABSTRACT

Certain m-dioxane-5-methylamines are useful analgesic agents and intermediate 2-substituted-1,3-propanediols are useful in the preparation of such compounds.

4 Claims, No Drawings

1,3-PROPANDIOL INTERMEDIATES

CROSS REFERENCE TO RELATED APPLICATION

This is a division, of application serial no. 427,944 filed Dec. 26, 1973 which is in turn a continuation-in-part of application, Ser. No. 313,221 filed Dec. 8, 1972. now abandoned.

BACKGROUND OF THE INVENTION

This invention relates to m-dioxane-5-methylamines and their pharmaceutically acceptable acid-addition salts having analgesic activity as well as the 2-substituted-1,3-propanediols which are useful intermediates in the preparation of such compounds.

In equianalgesic doses, morphine and its synthetic surrogates produce approximately the same incidence and degree of unwanted side effects. Nevertheless, there are some patients who may have side effects with one agent and not with another; therefore the surrogates are useful additions to the therapeutic regimen. When the pain is likely to be of short duration (e.g. diagnostic procedures, cystoscopy, orthopedic manipulations, etc.) a drug with a shorter duration of action might be preferable to morphine or methadone.

It is a purpose of this invention to provide m-dioxane-5-methylamines and their pharmaceutically-acceptable salts having analgesic activity. Many of the instant compounds have analgesic activity of short duration with minimal untoward side effects such as tolerance or physical dependence.

Several compounds containing a 1,3-dioxolane nucleus in their chemical structure are reported to have analgesic activity. Dexoxadrol, d-2,2-diphenyl-4-(2-piperdyl)-1,3-dioxolane hydrochloride, is a mild analgesic with a high incidence of psychotomimetic side effects [Lasagna and Pearson, *Proc. Soc. Exp. Biol. N.Y.* 118, 352 (1965)]. N,N,2-Trimethyl-1,3-dioxolane-4-methylamine is a mild analgesic with cholinergic side effects [McClure, *Arch. int. Pharmacodyn.* 179, 154 (1969)].

SUMMARY OF THE INVENTION

The compounds provided by this invention are represented by the following general formula

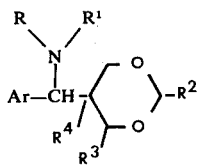

wherein
R represents hydrogen, $C_1$-$C_4$ alkyl, $C_3$-$C_4$ alkenyl or benzyl;
$R^1$ represents $C_1$-$C_4$ alkyl, $C_3$-$C_4$ alkenyl or benzyl;
R and $R^1$ when taken together with the nitrogen atom to which they are attached represent aziridino, pyrrolidino or piperidino;
$R^2$ represents hydrogen, $C_1$-$C_3$ alkyl, $C_2$-$C_3$ alkenyl or phenyl;
$R^3$ and $R^4$ represent hydrogen or methyl; and
Ar represents phenyl, halophenyl, hydroxyphenyl, mehoxyphenyl, methylphenyl, trifluoromethylphenyl or 3-pyridyl;
subject to the limitations that (a) $R^2$ is hydrogen when $R^3$ is methyl, (b) only one of $R^3$ and $R^4$ is methyl, and (c) Ar is other than 3-pyridyl when $R^3$ is methyl;
and the pharmaceutically acceptable acid-addition salts thereof.

The present invention is also directed to the intermediate 2-substituted-1,3-propanediol compounds represented by the formula

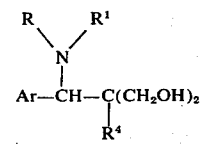

wherein Ar, R, $R^1$ and $R^4$ have the above-defined meanings.

The compounds of the invention are prepared by a variety of different methods. The N,N-disubstituted-m-dioxane-5-methylamine compounds are prepared via condensation of the appropriate aromatic aldehyde with a malonic ester (Knoevenagel condensation), Michael addition of secondary amines ($RR^1NH$) to the Knoevenagel intermediate to provide a 2-(substituted)aminomethyl malonic ester, chemical reduction of the ester to provide a 2-(substituted) aminomethyl-1,3-propanediol, and condensation of the diol with the appropriate aldehydes in the presence of boron trifluoride.

The N,N-disubstituted-5-methyl-m-dioxane-5-methylamine compounds are prepared via alkylation of the appropriate iminium salt with the sodium salt of diethyl methylmalonate to provide intermediates 2-(substituted)aminomethyl methylmalonate esters, reduction of the esters to provide 2-(substituted)aminomethyl-2-methyl-1,3-propanediols, and condensation of the diols with aldehydes ($R^2CHO$).

The N,N-disubstituted-4-methyl-m-dioxane-5-methylamine compounds, exclusive of the 3-pyridyl compounds, are prepared via an enamine reaction of 5-aroyl-4-methyl-m-dioxanes with secondary amines ($RR^1NH$) followed by reduction.

The N-alkyl-m-dioxane-5-methylamine compounds are obtained by reductive debenzylation of the corresponding N-alkyl-N-benzyl-m-dioxane-5-methylamine commpounds.

The N-alkenyl-m-dioxane-5-methylamine compounds are prepared by the chemical reduction of the corresponding N-alkenamido-m-dioxane-5-methylamine compounds.

Alternatively, the compounds of the invention can be prepared by alkylation of the appropriate m-dioxane-5-methylamines which are available from the N,N-dibenzyl-m-dioxane-5-methylamine compounds by reductive debenzylation or from the appropriate 5-aroyl-4(5)-m-dioxane-oximes by reduction.

The intermediate 2-substituted-1,3-propanediols prepared by chemical reduction of the corresponding 2-(substituted)aminoethyl malonic esters with lithium aluminum hydride (LAH) or sodium bis-(2-methoxyethoxy)alumonum hydride in an aprotic solvent such as benzene or tetrahydrofuran.

The substituted 1,3-propanediol compounds are reacted with formaldehyde, formaldehyde polymer, acetaldehyde, propionaldehyde, butyraldehyde, acrylaldehyde, crotonaldehyde, benzaldehyde, and the like, to provide the analgesic compounds of the invention.

The amines of the present invention are named as recommended by Chemical Abstracts [The Naming and Indexing of Chemical Compounds, section 259]. Cyclic compounds in which the amino group is separated from the ring (dioxane) by an aliphatic chain are named by the use of a conjunctive name, for example, m-dioxane-5-methylamine. The Greek letter α is used to indicate the position next to the amino group.

DETAILED DESCRIPTION

The m-dioxane-5-methylamines of the present invention are represented by the following formula

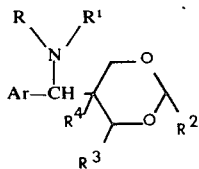

I wherein
R is hydrogen, $C_1$-$C_4$ alkyl, $C_3$-$C_4$ alkenyl or benzyl;
$R^1$ is $C_1$-$C_4$ alkyl, $C_3$-$C_4$ alkenyl or benzyl;
R and $R^1$, when taken together with the nitrogen atom to which they are attached, are aziridino, pyrrolidino or piperidino;
$R^2$ is hydrogen, $C_1$-$C_3$ alkyl, $C_2$-$C_3$ alkenyl or phenyl;
$R^3$ and $R^4$ are hydrogen or methyl; and
Ar is phenyl, halophenyl, hydroxyphenyl, methoxyphenyl, methylphenyl, trifluoromethylphenyl or 3-pyridyl;
with the limitations that (a) $R^2$ is hydrogen when $R^3$ is methyl, (b) only one of $R^3$ and $R^4$ is methyl, and
(c) Ar is other than 3-pyridyl when $R^3$ is methyl;
and the pharmaceutically-acceptable acid-addition salts thereof.

The present invention is also directed to the intermediate 2-substituted-1,3-propanediol compounds represented by

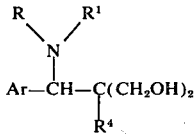

II wherein Ar, R, $R^1$ and $R^4$ have the above-defined meanings.

As used herein, the term "$C_1$-$C_4$ alkyl" refers to methyl, ethyl, propyl, isopropyl, n-butyl, iso-butyl, sec-butyl and tert-butyl. The term "$C_3$-$C_4$ alkenyl" refers to allyl, methallyl, 2-butenyl and like groups.

The term halophenyl refers to phenyl substituted by halogen such as 2-chlorophenyl, 4-chlorophenyl, 2,4-dichlorophenyl, 4-fluorophenyl, 3-iodophenyl and 4-iodophenyl. Methylphenyl refers to phenyl substituted by methyl such as 2-methylphenyl, 3-methylphenyl, and 4-methylphenyl. Trifluoromethylphenyl refers to phenyl substituted by trifluoromethyl such as 2-trifluoromethylphenyl and 4-trifluoromethylphenyl. Methoxyphenyl refers to phenyl substituted by methoxy such as 3-methoxyphenyl, 4-methylphenyl and 3,4-dimethoxyphenyl. Hydroxyphenyl refers to phenyl substituted by hydroxy such as 3-hydroxyphenyl, 4-hydroxyphenyl and 3,4-dihydroxyphenyl.

The pharmaceutically-acceptable acid-addition salts of the amino compounds of this invention are included within the scope of this invention. "Pharmaceutically-acceptable" salts are those salts formed from acids which do not increase the toxicity of the compound as a whole toward warm-blooded animals. Otherwise the identify of the salt-forming moiety is not critical, although in some instances a given anion may exhibit special advantage, such as ready solubility, ease of crystallization, and the like. Representative and suitable acids include the mineral acids such as hydrochloric, hydrobromic, hydriodic, sulfuric, phosphoric, nitric, and like acids, and carboxylic acids such as acetic, citric, maleic, tartaric, and the like.

The compounds of the invention are prepared by a variety of different methods. Each method providing a specific type of m-dioxane-5-methylamine compound is described hereinafter in detail.

The N,N-disubstituted-m-dioxane-5-methylamine compounds generally are prepared by (a) condensation of an appropriate aromatic aldehyde with a malonic ester via the Knoevenagel condensation, (b) reaction of the intermediate Knoevenagel product with an appropriate secondary amine ($RR^1NH$) via a Michael addition to provide a 2-(substituted)aminomethyl malonic ester, (c) chemical reduction of the intermediate ester to provide a 2-(substituted) aminomethyl-1,3-propanediol and, (d) condensation of the substituted 1,3-propanediol with the appropriate aldehyde in the presence of boron trifluoride. This preparative sequence is illustrated in reaction Scheme I, below:

Scheme I. Preparation of N,N-disubstituted-m-dioxane-5-methylamines (a) Knoevenagel condensation
Ar—CHO + $CH_2(CO_2C_2H_5)_2$ → $ArCH=C(CO_2C_2H_5)_2$ (b) Michael addition
$ArCH=C(CO_2C_2H_5)$ + $HNRR^1$ → $ArCH(NRR^1)CH(CO_2C_2H_5)_2$ (c) Reduction          LAH
$ArCH(NRR^1)CH(CO_2C_2H_5)_2$ → $ArCH(NRR^1)CH(CH_2OH)_2$ (d) Aldehyde condensation $ArCH(NRR^1)CH(CH_2OH)_2 + R^2CHO →$ 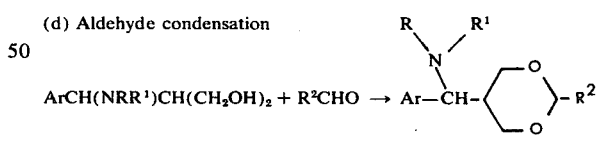

When 3-pyridinecarboxaldehyde is used in the Knoevenagel condensation, the product is an α-(3-pyridyl)-m-dioxane-5-methylamine.

The Michael addition does not conveniently lend itself to the use of primary amines and operates best with secondary amines. Representative amines which can be employed are dimethylamine, dipropylamine, dibutylamine, diisopropylamine, diisobutylamine, diallylamine, N-methylbenzylamine, dibenzylamine, N-ethylbenzylamine, bis-(2-methylallyl)amine, N-butyl-tert-butylamine, N-isopropylbenzylamine and the like. Secondary amines which are not commercially available can be prepared from the appropriate N-substituted aliphatic amides. For example, reduction of N-isopropylacrylamide with lithium aluminum hydride provides N-isopropylallylamine. N-alkylbenzylamines are obtained by the reduction of the precursor Schiff bases.

Because of the limitations of the Michael addition, the N-monosubstituted-m-dioxane-5-methylamines or the dioxane primary amines are prepared in an indirect manner, using N-(alkyl)benzylamines or dibenzylamine in the Michael addition. The resulting N-alkyl-N-benzyl- or N,N-dibenzyl-m-dioxane-5-methylamines are reductively benzylated in an amphiprotic solvent such as, for example, 95 percent ethanol, under hydrogen pressures of from 15 to 60 psi using palladium-on-carbon or platinum [see R. B. Wagner and H. D. Zook, "Synthetic Organic Synthesis," John Wiley, New York, N. Y., 1965, pg. 665]. The products of debenzylation are N-alkyl-m-dioxane-5-methylamines or dioxane primary amines, respectively.

The N,N-disubstituted-5-methyl-m-dioxane-5-methylamine compounds are prepared by (a) alkylation of the appropriate iminium salt with the sodium salt of diethyl methylmalonate to provide an intermediate 2-(substituted)aminomethyl methylmalonic ester, (b) chemical reduction of the ester to provide a 2-(substituted) aminomethyl-2-methyl-1,3-propanediol and (c) condensation of the substituted 2-methyl-1,3-propanediol with the appropriate aldehyde in the presence of boron trifluoride. This process provides compounds which bear a methyl group on the 5-position of the dioxane ring and is illustrated in reaction Scheme II, below:

Scheme II. Preparation of N,N-disubstituted-5-methyl-m-dioxane-5-methylamines (a) Iminium salt alkylation

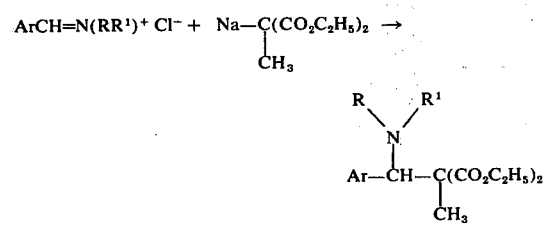

(b) Reduction

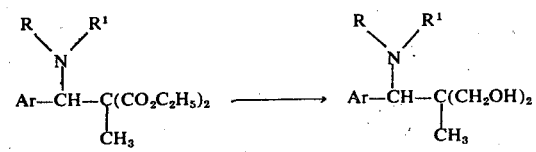

(c) Aldehyde condensation

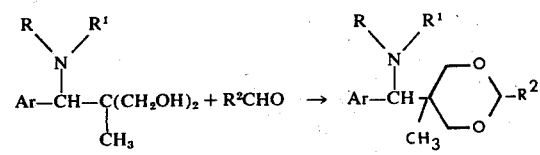

The iminium salts required for this method of synthesis are prepared as described by Leonard, N. J. and Paukstelis, J. V., J. Org. Chem. 28, 3021(1963) and Hauser, C. R. and Stewart, A. T., J. Am. Chem. Soc. 77, 1098(1955).

The following illustrates the use of iminium salts in the preparation of the compounds of the invention. α-Dimethylaminobenzyl n-butyl ether is prepared by reacting benzaldehyde, n-butanol and anhydrous dimethylamine in the presence of potassium carbonate by the method of Hauser, C. R., et al., J. Am. Chem. Soc., 77. 1098(1955). The butyl ether is cleaved in ether saturated with anhydrous hydrogen chloride to provide N-benzylidenedimethylaminium chloride. The iminium salt is reacted with sodium diethyl methylmalonate, prepared from diethyl methylmalonate and sodium hydride [see Bohme, H., et al., Chem. Ber., 92, 2976(1959)]. The product is recovered as described by Bohme to provide diethyl 2-α-dimethylaminobenzyl-2-methylmalonate. The ester is reduced with lithium aluminum hydride or sodium bis-(2-methoxyethoxy)aluminum hydride to yield 2-α-dimethylaminobenzyl-2-methyl-1,3-propanediol. The propanediol is reacted with paraformaldehyde to provide N,N,5-trimethyl-α-phenyl-m-dioxane-5-methylamine. When 3-pyridinecarboxyaldehyde is used to provide the iminium salt, the product is an α-(3-pyridyl)-5-methyl-m-dioxane-5-methylamine.

The N,N-disubstituted-4-methyl-m-dioxane-5-methylamine compounds, exclusive of 3-pyridyl compounds, are prepared via an enamine reaction. A 5-aroyl-4-methyl-m-dioxane is reacted with the appropriate secondary amine to provide an enamine which is reduced with hydrogen in the presence of a catalyst or with sodium borohydride in acetic acid [See Marshall, J. A. and Johnson, W. S., J. Org. Chem. 28, 421(1963)]. The enamine process is illustrated below in reaction Scheme III.

Scheme III. Preparation of α-aryl-N,N-disubstituted-4-methyl-m-dioxane-5-methylamines

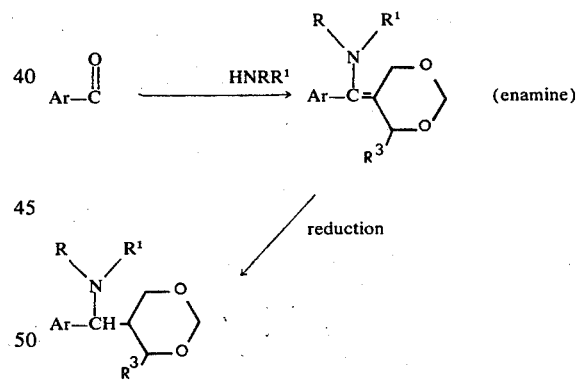

A 5-aroyl-m-dioxane can be employed in the enamine process to provide a compound without a 4-methyl substituent.

5-Benzoyl-m-dioxane and 5-benzoyl-4-methyl-m-dioxane, illustrative of the 5-aroyl-m-dioxanes required in the enamine method of synthesis, are available by the known reaction of acetophenones or phenylpropenyl ketones with formaldehyde or formaldehyde polymer in the presence of boron trifluoride [(a) Terada, Nippon Kagan Zasshi., 81, 612(1960). Chem. Abstr. 56, 1446(1962), (b) British Patent 1,148,247; Chem. Abstr. 71, 61394u (1969); (c) Wesslen, Acta. Chem. Scand., 23 1033(1969)].

An alternate method for preparing the compounds exclusive of the 3-pyridyl derivatives which bear a methyl substituent on the 4- or 5-position of the dioxane moiety begins with the oxime of the appropriate 5-aroyl-4(5)-methyl-m-dioxane. The 5-aroyl-5-methyl-m-dioxane is available from propiophenone and formaldehyde as described hereinabove. The oxime is reduced catalytically or chemically with LAH to provide a 4(5)-methyl-m-dioxane-5-methylamine. If the dioxane primary amine is reacted with formaldehyde in the presence of formic acid (Eschweiler-Clarke reaction), the product is an N,N-dimethyl-4(5)-methyl-m-dioxane-5-methylamine. If, on the other hand, the dioxane primary amine is reacted with benzaldehyde to produce a Schiff base and the base is reduced, the product is an N-benzyl-4(5)-methyl-m-dioxane-5-methylamine. The N-benzyl intermediate can be N-alkylated with an alkyl halide to provide an N-alkyl-N-benzyl-4(5)-methyl-m-dioxane-5-methylamine. The product can be reductively debenzylated as described hereinabove to provide an N-alkyl-4(5)-methyl-m-dioxane-5-methylamine compound. Subsequently, the debenzylated product can be alkylated again with an alkyl- or alkenyl halide to provide an N-alkyl-N-alkyl-(alkenyl)-4(5)-methyl-m-dioxane-5-methylamine. The oxime preparative sequence is illustrated below in reaction Scheme IV.

Scheme IV, Preparation of α-aryl-N,N-substituted-4(5)-methyl-m-dioxane-5-methylamines

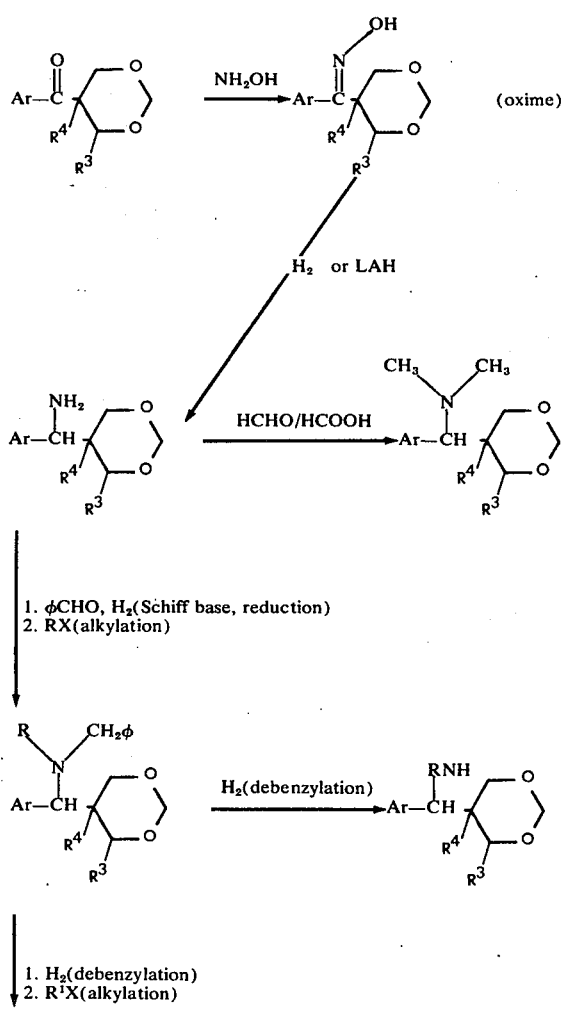

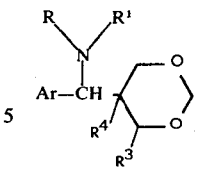

The reductive debenzylation method cannot be applied in the presence of alkenyl groups. Therefore, the N-alkenyl-m-dioxane-5-methylamine compounds are prepared from the corresponding dioxane primary amines. The required dioxane primary amines are available from the oximes by reduction or from the N,N-dibenzyl intermediates by exhaustive reductive debenzylation. Since alkylation of primary amines generally produces mixtures of mono- and dialkylated products, an alternative method is preferred. The appropriate dioxane primary amine is acylated with an alkenyl acid chloride, such as acryloyl chloride, crotonyl chloride or the like, to provide the corresponding N-alkenamido-m-dioxane-5-methylamine. The N-alkenamide intermediate is reduced chemically with lithium aluminum hydride (LAH), for example, to provide the desired N-alkenyl-m-dioxane-5-methylamine. It will be noted that this method of preparation is not limited to the use of alkenyl acid chlorides. The use of $C_2$-$C_4$ alkyl acid chlorides will give N-alkanamido-m-dioxane-5-methylamine compounds which can be reduced to provide N-alkyl-m-dioxane-5-methylamine compounds, if desired.

In addition, it will be apparent that monodebenzylation of N,N-dibenzyl compounds will provide N-benzyl-m-dioxane-5-methylamine intermediates which can be alkylated and debenzylated to provide N-alkyl-m-dioxane-5-methylamine compounds. N,N-disubstituted compounds with the same or different N-substituent groups can also be prepared from N-alkyl- or N-alkenyl-m-dioxane-5-methylamine compounds by alkylation with alkyl- or alkenyl halides or by repeating the acylation and reduction procedure described above.

Still another method can be employed to provide specifically the N-methyl-m-dioxane-5-methylamine compounds from the corresponding N,N-dimethyl analogs by demethylation in the presence of diethyl azodicarboxylate.

The present invention is also directed to the intermediate 2-substituted-1,3-propanediols, which are condensed with aldehydes to provide the m-dioxane-5-methylamines. The propanediols are obtained, as already noted, by chemical reduction of the corresponding 2-substituted malonic esters. However prepared, the 2-substituted-1,3-propanediol compounds are reacted with the appropriate aldehydes, exemplified by formaldehyde or formaldehyde polymer, acetaldehyde, propionaldehyde, butyraldehyde, acrylaldehyde, crotonaldehyde, benzaldehyde and the like, in the presence of boron trifluoride to provide the analgesic compounds of the invention.

The N-benzyl and N,N-dibenzyl-m-dioxane-5-methylamine compounds do not themselves possess significant analgesic activity. They are, however, useful in preparing m-dioxane-5-methylamine compounds having analgesic properties by the procedures outlined above. Those compounds wherein the α-substituent is a 3-hydroxyphenyl, 4-hydroxyphenyl or 3,4-dihydroxyphenyl are prepared by cleaving the ether group of the corresponding 3-methoxyphenyl, 4-methoxyphenyl or 3,4-dimethoxyphenyl compound with pyridine hydrochloride, aluminum chloride or the lithium salt of diphenylphosphide as described by Fieser and Fieser in "Reagents For Organic Synthesis," John Wiley and Sons, Inc., New York, N. Y., 1967.

The m-dioxane-5-methylamine compounds prepared from the condensations with formaldehyde, acetaldehyde and propionaldehyde are preferred. A further preferred group are those wherein the α-substituent is chosen from among phenyl, 4-methylphenyl and 3-pyridyl. The most preferred compounds are those wherein the amine group is dimethylamino. Exemplary of the preferred compounds provided by this invention are the following:

N,N-dimethyl-α-phenyl-m-dioxane-5-methylamine,
N,N-dimethyl-α-phenyl-2-methyl-m-dioxane-5-methylamine,
N,N-dimethyl-α-phenyl-2-ethyl-m-dioxane-5-methylamine,
N,N-dimethyl-α-(4-methylphenyl)-m-dioxane-5-methylamine,
N,N-dimethyl-α-(4-methylphenyl)-2-methyl-m-dioxane-5-methylamine,
N,N-dimethyl-α-(4-methylphenyl)-2-ethyl-m-dioxane-5-methylamine,
N,N-dimethyl-α-(3-pyridyl)-m-dioxane-5-methylamine,
N,N-dimethyl-α-(3-pyridyl)-2-methyl-m-dioxane-5-methylamine,
N,N-dimethyl-α-(3-pyridyl)-2-ethyl-m-dioxane-5-methylamine, and the pharmaceutically-acceptable salts thereof.

The pharmaceutically-acceptable salts can be prepared by neutralization of the dioxane amine in solution with the appropriate acid. They can be prepared from mineral acids such as hydrobromic, hydrochloric, nitric, phosphoric, sulfuric and the like acids. Salts of organic acids can be prepared from carboxylic acids such as acetic, citric, maleic, tartaric and the like.

It will be noted that the analgesic compounds of the invention possess at least one asymmetric carbon atom, the α-carbon atom. Accordingly, at least two different forms of each compound are possible, those consisting of an enantiomeric pair which can be resolved into dextro- and levorotatory isomers. When subsitution is present in the 4-position of the m-dioxane ring, two additional asymmetric carbons are present. In such a situation eight different forms of each compound are possible. The optical resolution of such mixtures provides the analgesically active pure enantiomers. The resolution of an analgesic compound with three asymmetric centers is a major task which involves the separation of four diastereoisomeric pairs. While it is preferable to employ the pure isomers as analgesics, the racemic mixtures are useful for the purpose mentioned herein in accordance with their analgesic content. All the compounds of the present invention demonstrate analgesic activity as racemic mixtures. It will be understood by those skilled in the art that in such mixtures, pharmacological activity may frequently reside to a greater degree, or entirely, in one of the stereoisomeric forms.

In a preferred embodiment of the present invention, dl-N,N-dimethyl-α-phenyl-m-dioxane-5-methylamine is resolved to provide the analgesically active 1-N,N-dimethyl-α-phenyl-m-dioxane-5-methylamine by the use of dibenzoyl-1-tartaric acid monohydrate. The resolved solid 1-amine is taken up in ether and treated with gaseous hydrogen chloride to provide pure 1-N,N-dimethyl-α-phenyl-m-dioxane-5-methylamine hydrochloride after recrystallization from methanol-ethyl acetate.

Analgesic activity for representative compounds of the instant invention was determined with two standard animal techniques. The mouse writhing assay used was a modification of the method wherein frequency of writhing [Hendershot and Sorsaith, J. Pharm. Exp. Ther. 125, 237 (1959)] is observed after intra peritoneal administration of 0.6 percent acetic acid [Koster et al., Fed. Proc. Soc. Expt. Biol. 18, 412 (1959)]. The mice were Cox standard males weighting 20–22 gm. The number of writhes was determined for each of five mice during the period 5–15 minutes after acetic acid treatment. The percent inhibition due to drug treatment was determined by comparison with control mice.

The other analgesic method was the rat tail jerk assay described by Robbins, J. Amer. Pharm. Assoc. Sci. Ed., 44, 497 (1955). The rats were Sprague-Dawley females weighing 70–90 g. Briefly, the tail was held on a temperature controlled tail rest near a nichrome resistance wire through which a current could flow. A switch used to start the flow of current to heat the wire simultaneously started a timer. When a jerk of the tail was detected by the operator, the switch was released and the latency of the response was recorded as the "reaction time." The tail was placed near the hot wire stimulus for a maximum duration of 30 seconds. Twenty rats were tested as a group in a randomized order. At least five rats were used for each treatment and each rat was dosed and tested only once.

Table 1 below gives the results of testing representative compounds of this invention as analgesics by the above methods. The first four columns in Table 1 describe the particular compound tested. The next eight columns give the mouse writhing results and the rat tail jerk results both by oral and subcutaneous administration. The columns headed PT ("Peak Analgesic Time") give the time in minutes after dosing at which the maximum analgesic responses are measured. The columns headed "$ED_{50}$ (mg./kg.)" give the doses ($ED_{50}$) in milligrams per kilogram (mg./kg.) of body weight that produce a significant peak analgesic effect in 50 percent of test animals.

Table 1

In Vivo Analgesic Activity of
m-dioxane-5-methylamines

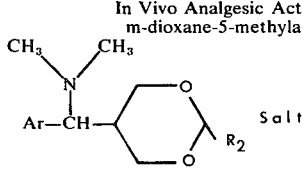

| Formula | | | Mouse Writhing | | | | Rat Tail Jerk | | | |
| | | | Subcutaneous | | Oral | | Subcutaneous | | Oral | |
| form | Ar | $R^2$ | Salt | PT* (min.) | $ED_{50}$ (mg./kg.) | PT (min.) | $ED_{50}$ (mg./kg.) | PT (min.) | $ED_{50}$ (mg./kg.) | PT (min.) | $ED_{50}$ (mg./kg.) |
|---|---|---|---|---|---|---|---|---|---|---|---|
| dl | $C_6H_5$ | H | HCl | 15 | 15 | 45 | 28 | 15 | 4.5 | 15 | 27 |
| l | $C_6H_5$ | H | HCl | 15 | 6 | 15 | 16 | 15 | 7.0 | 15 | 10 to 20 |
| dl | 4-$CH_3$—$C_6H_4$ | H | Maleate | 30 | 20 | 45 | 110 | 30 | 8.0 | 45 | 60 |
| dl | $C_6H_5$ | $CH_3$ | ** | 15 | 3.6 | 15 | 19 | 20 | 2.8 | 15 | 12 |
| dl | $C_6H_5$ | $C_2H_5$ | ** | 75 | 19 | 75 | 23 | 15 | 3.4 | 15 | 21 |
| dl | 3-pyridyl | H | 2HCl | 30 | 10 | 30 | 25 | 15 | 7.0 | 15 | 7.0 |

*PT is the peak analagesic time in minutes
**Free base tested

Other compounds coming within the scope of this invention have a comparable analgesic activity although the dose required to produce analgesic activity varies from compound to compound. In addition, the time of peak analgesic action will vary somewhat from compound to compound. Many of the compounds of this invention are short acting, which is an advantage when pain is likely to be of short duration; however, 2-ethyl-N,N-dimethyl-α-phenyl-m-dioxane-5-methylamine is long acting in mice. The instant compounds are relatively non-toxic in that their analgesically effective dose is low compared to the dose at which toxic signs appear.

Since the compounds of this invention are effective analgesics by the oral route, this route of administration is preferred. The instant compounds can be administered at a nontoxic dose between about 1 and 200 mg./kg. of body weight as a single dose or as multiple doses until the desired therapeutic result is achieved. For oral administration, the compound may be placed in empty telescoping gelatine capsules, either with or without conventional pharmaceutical extending media. The compounds can also be mixed with various excipients, binders, etc. and compressed into tablets. Additionally, it is also possible to administer the compounds orally in a suspension or in aqueous solutions of their acid-addition salts.

Illustrative of the m-dioxane-5-methylamines which are provided by this invention are the following:

2-allyl-N,N-dimethyl-α-phenyl-m-dioxane-5-methylamine,
N-allyl-α-phenyl-m-dioxane-5-methylamine,
2-allyl-N,N-dimethyl-α-(3-pyridyl)-m-dioxane-5-methylamine,
N-allyl-α-phenyl-m-dioxane-5-methylamine,
N-allyl-α,2-diphenyl-m-dioxane-5-methylamine,
-α-(4-benzyloxyphenyl)-N,N-dimethyl-m-dioxane-5-methylamine,
N,N-di-2-butenyl-α-phenyl-m-dioxane-5-methylamine,
N,N-dimethyl-α-(4-chlorophenyl)-m-dioxane-5-methylamine,
N,N-dibutyl-α-phenyl-m-dioxane-5-methylamine,
N,N-dimethyl-α-(2,4-dichlorophenyl)-m-dioxane-5-methylamine,
N,N-dimethyl-α,2-diphenyl-m-dioxane-5-methylamine,
N,N-dimethyl-α-(4-trifluoromethylphenyl)-m-dioxane-5-methylamine,
N,N-dimethyl-α-(4-fluorophenyl)-m-dioxane-5-methylamine,
N,N-dimethyl-α-(4-hydroxyphenyl)-m-dioxane-5-methylamine,
N,N-dimethyl-α-(3-methoxyphenyl)-m-dioxane-5-methylamine,
N,N-dimethyl-2-isopropyl-α-phenyl-m-dioxane-5-methylamine,
1-[α-(m-dioxan-5-yl)benzyl]aziridine,
1-[α-(m-dioxan-5-yl)-(4-chlorobenzyl)]piperidine,
1-[α-(m-dioxan-5-yl)benzyl]pyrrolidine,
N,2-diallyl-α-phenyl-m-dioxane-5-methylamine,
N,N-dimethyl-2-ethyl-α-(3-pyridyl)-m-dioxane-5-methylamine,
N,N-dimethyl-2-phenyl-α-(3-pyridyl)-m-dioxane-5-methylamine,
1-[α-(m-dioxan-5-yl)-(3-pyridyl)methyl]aziridine,
N,N-dibutylamino-α-(3-pyridyl)-m-dioxane-5-methylamine,
N-methyl-N-butyl-α-phenyl-m-dioxane-5-methylamine,
N-methyl-N-ethyl-α-phenyl-m-dioxane-5-methylamine,
N-methyl-α-phenyl-m-dioxane-5-methylamine,
N,N,5-trimethyl-α-phenyl-m-dioxane-5-methylamine,
N,N,2,5-tetramethyl-α-phenyl-m-dioxane-5-methylamine,
N,N,5-trimethyl-α-(3-pyridyl)-m-dioxane-5-methylamine,
N,N2,5-tetramethyl-α-(3-pyridyl)-m-dioxane-5-methylamine,
1-[α-(4-methyl-m-dioxane-5-yl)-benzyl]aziridine,
1-[α-(5-methyl-m-dioxan-5yl)benzyl]aziridine,
1-[α-(5-methyl-m-dioxan-5-yl)-3-pyridylmethyl]aziridine,
1-[α-(4-methyl-m-dioxan-5-yl)benzyl]pyrrolidine,
1-[α-(5-methyl-m-dioxan-5-yl)benzyl]pyrrolidine,
1-[α-(5-methyl-m-dioxan-5-yl)-3-pyridylmethyl]pyrrolidine,
1-[α-(4-methyl-m-dioxan-5-yl)benzyl]piperidine,
1-[α-(5-methyl-m-dioxan-5-yl)benzyl]piperidine, 1-[α-(5-methyl-m-dioxan-5-yl)-3-pyridylmethyl]-piperidine,
1-[α-(2,5-dimethyl-m-dioxan-5-yl)benzyl]aziridine,
1-[α-(2,5-dimethyl-m-dioxan-5-yl)-3-pyridylmethyl]aziridine,
1-[α-(2,5-dimethyl-m-dioxan-5-yl)benzyl]pyrrolidine,
1-[α-(2,5-dimethyl-m-dioxan-5-yl)-3-pyridylmethyl]pyrrolidine,
1-[α-(2,5-dimethyl-m-dioxan-5-yl)benzyl]piperidine,
1-[α-(2,5-dimethyl-m-dioxan-5-yl)-3-pyridylmethyl]piperidine,
N,N,5-trimethyl-α,2-diphenyl-m-dioxane-5-methylamine,
1-[α-(5-methyl-2-phenyl-m-dioxan-5-yl)benzyl]aziridine,
N-methyl-α-(3-pyridyl)-m-dioxane-5-methylamine,
N,N,4-trimethyl-α-(3-pyridyl)-m-dioxane-5-methylamine,
N,N,5-trimethyl-α-(3-pyridyl)-m-dioxane-5-methylamine,
1-[α-(m-dioxan-5-yl)-(3-pyridyl)methyl]aziridine,
1-[α-(m-dioxan-5-yl)-(3-pyridyl)methyl]piperidine,
1-[α-(m-dioxan-5-yl)-(3-pyridyl)methyl]pyrrolidine,
N,N,2-triallyl-α-phenyl-m-dioxane-5-methylamine,
N,N,2-triallyl-α-(3-pyridyl)-m-dioxane-5-methylamine,
N,N-dimethyl-2-phenyl-α-(3-pyridyl)-m-dioxane-5-methylamine,
1-[α-(2-ethyl-m-dioxan-5-yl)benzyl]aziridine,
1-[α-(2-ethyl-m-dioxan-5-yl)-(3-pyridyl)methyl]pyrrolidine,
and the pharmaceutically-acceptable acid-addition salts thereof.

Illustrative of the intermediate 2-substituted-1,3-propanediol compounds provide by this invention are the following:

2-α-(1-aziridinyl)benzyl-1,3-propanediol,
2-α-(1-pyrrolidinyl)benzyl-1,3-propanediol,
2-α-(4-piperidinyl)benzyl-1,3-propanediol,
2-α-(1-aziridinyl)benzyl-3-methyl-1,3-propanediol,
2-α-(1-pyrrolidinyl)benzyl-2-methyl-1,3-propanediol,
2-α-(4-piperidinyl)benzyl-2-methyl-1,3-propanediol,
2-[α-(1-aziridinyl)-3-pyridylmethyl]-1,3-propanediol,
2-[α-(1-pyrrolidinyl)-3-pyridylmethyl]-1,3-propanediol,
2-[α-(4-piperidinyl)-3-pyridylmethyl]-1,3-propanediol,
2-[α-(1-aziridinyl)-3-pyridylmethyl]-2-methyl-1,3-propanediol,
2-[α-(1-pyrrolidinyl)-3-pyridylmethyl]-2-methyl-1,3-propanediol,
2-[α-(4-piperidinyl)-3-pyridylmethyl]-2-methyl-1,3-propanediol,
2-α-dibenzylaminobenzyl-1,3-propanediol,
2-α-dibenzylaminobenzyl-2-methyl-1,3-propanediol,
2-α-dimethylaminobenzyl-2-methyl-1,3-propanediol,
2-α-(N-allyl-N-methylamino)benzyl-2-methyl-1,3-propanediol,
2-α-diallylaminobenzyl-1,3-propanediol,
2-α-(N-allyl-N-2-butenylamino)benzyl-2-methyl-1,3-propanediol,
2-(α-dibenzylamino-3-pyridylmethyl)-1,3-propanediol,
2-(α-dibenzylamino-3-pyridylmethyl)-2-methyl-1,3-propanediol,
2-[α-(N-alkyl-N-methylamino)-3-pyridylmethyl]-1,3-propanediol,
2-(α-dimethylamino-3-pyridylmethyl)-2-methyl-1,3-propanediol,
2-(α-diallylamino-3-pyridylmethyl)-1,3-propanediol,
2-[α-(N-allyl-N-methylamino)-3-pyridylmethyl]-2-methyl-1,3-propanediol,
2-[α-(N-2-butenyl-N-methylamino)-3-pyridylmethyl]-1,3-propanediol.

EXAMPLE 1

Preparation of Diethyl Benzalmalonates

Diethyl benzalmalonate.

Two moles, 212 g., of benzaldehyde, 320 g. (2.0 moles) of diethyl malonate and 10 ml. of piperidine were refluxed in 400 ml. of benzene. The theoretical amount of water was collected in a Dean-Stark trap by azeotropic distillation in about 7 hours. The reaction mixture was poured into water after cooling. The aqueous mixture was extracted with ether and the extract was washed successively with saturated sodium bisulfite solution, water, saturated sodium bicarbonate solution and finally water. The extract was dried over anhydrous magnesium sulfate and the ether was evaporated to leave an oil. The oil was distilled and the fraction, bp 140°C. (0.1 mm), was collected to yield 343 g. of diethyl benzalmalonate.

The following substituted diethyl benzalmalonates were prepared using the procedure of example 1 with the appropriate aromatic aldehyde:

Table 2

Diethyl Benzalmalonates

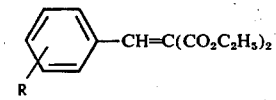

| R | bp, C°(mm.) | Calculated C | H | Cl | Found C | H | Cl |
|---|---|---|---|---|---|---|---|
| 2-CH₃ | 142 (0.7) | 68.68; | 6.92 | | 68.79; | 7.10 | |
| 3-CH₃ | 138 (0.7) | 68.68; | 6.92 | | 68.66; | 7.12 | |
| 3-CH₃O | 154 (0.7) | 64.73; | 6.52 | | 64.43; | 6.63 | |
| 4-CH₃O | 162 (0.7) | 64.73; | 6.52 | | 64.60; | 6.49 | |
| 2-Cl | 142 (0.7) | 59.26; | 5.68 | | 59.48; | 5.39 | |
| 3-Cl | 150 (0.7) | 59.26; | 5.68 | | 59.55; | 5.51 | |
| 4-Cl | 144 (0.7) | 59.26; | 5.68 | | 59.53; | 5.77 | |
| 2,4-Cl₂ | 132 (0.05) | 53.01; | 4.45 | 22.36 | 50.47; | 4.21 | 21.6 |
| 4-F | 152 (0.05) | | | | | | |
| 4-φCH₂O | 210–222 (0.10) | | | | | | |

EXAMPLE 2

Preparation of Diethyl (α-substitutedamino)benzylmalonates

Diethyl (α-dimethylamino)benzylmalonate.- One hundred grams (2.2 moles) of anhydrous dimethylamine was dissolved in 200 ml. of ether and the mixture was cooled to 0°C. in an ice bath. Diethyl benzalmalonate, 200 g. (0.81 mole), in ether was added dropwise at a rapid rate to the cooled, stirred reaction mixture. The mixture was stirred at room temperature for 12 hours. The reaction mixture was evaporated in vacuo to give 240 g. of diethyl (α-dimethylamino)benzylmalonate.

In general the diethyl (α-dimethylamino)benzylmalonates were not purified prior to their use because of their relative instability. They were characterized by nuclear magnetic resonance spectrum (NMR). The following intermediates were prepared according to the method of Example 2:

diethyl(α-dibutylamino)benzylmalonate
diethyl(α-diethylamino)benzylmalonate
diethyl α-dimethylamino-(2-methylbenzyl)malonate
diethyl α-dimethylamino-(2-chlorobenzyl)malonate
diethyl α-dimethylamino-(4-chlorobenzyl)malonate
diethyl α-dimethylamino-(2,4-dichlorobenzyl)malonate
diethyl α-dimethylamino-(3-methoxybenzyl)malonate
diethyl α-dimethylamino-(4-methoxybenzyl)malonate
diethyl α-dimethylamino-(3-hydroxybenzyl)malonate
diethyl α-dimethylamino-(4-hydroxybenzyl)malonate
diethyl α-dimethylamine-(4-fluorobenzyl)malonate
diethyl (α-aziridino)benzylmalonate
diethyl (α-pyrrolidino)benzylmalonate
diethyl (α-piperidino)benzylmalonate

EXAMPLE 3

Preparation of 2-(α-substitutedamino)benzyl-1,3-propanediols 2-(α-Dimethylamino)benzyl-1,3-propanediol.

Sodium bis(2-methoxyethoxy)aluminum hydride, 450 ml. (1,6 mole), as a 70 percent solution in benzene, was dissolved in 200 ml. of dry benzene. The mixture was cooled in an ice bath. Diethyl (α-dimethylamino)benzylmalonate, 240 g. (0.81 mole), dissolved in 320 ml. of benzene, was added dropwise to the cold reaction mixture with stirring. The mixture was stirred for about 12 hours while the temperature was allowed to rise to room temperature. The reaction mixture was stirred into a mixture of ice and dilute sodium hydroxide solution. The resultant melt was extracted twice with ether. The ether extract was washed with water, dried over anhydrous magnesium sulfate and evaporated in vacuo. The residual oil was taken up in 100 ml. of ethyl acetate and diluted with 500 ml. of petroleum ether. The solution was concentrated by evaporation on the steam bath, and more petroleum ether was added to incipient turbidity. The mixture was cooled to induce crystallization. Eighty-five grams of 2-(α-dimethylamino)benzyl-1,3-propanediol, mp about 79°–80°C., was obtained.

The following 1,3-propanediols were prepared by the method of Example 3:

Table 3

1,3-propanediols

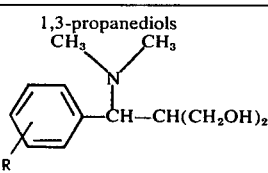

| R | mp, °C. | Calcd C | H | N | Found C | H | N |
| --- | --- | --- | --- | --- | --- | --- | --- |
| 2-CH₃ | (oil) | | | | | | |
| 3-CH₃ | 100 | 69.92; | 9.48; | 6.27 | 69.79; | 9.26; | 6.04 |
| 3-CH₃O | 92 | 65.25; | 8.85; | 5.85 | 65.26; | 8.81; | 5.59 |
| 4-CH₃O | 102 | 65.25; | 8.85; | 5.85 | 65.46; | 9.09; | 5.69 |
| 2-Cl | (oil) | | | | | | |
| 3-Cl | 90 | 59.13; | 7.44; | 5.75 | 59.34; | 7.74; | 5.97 |
| 4-Cl | 120 | 59.13; | 7.44; | 5.75 | 59.14; | 7.20; | 6.03 |
| 4-F | 85 | | | | | | |
| 2,4-Cl₂ | (oil) | | | | | | |
| 3-φCH₂O | 114 | 72.12; | 8.28; | 4.43 | 72.38; | 8.45; | 4.36 |
| 4-φCH₂O | 176 | | | | | | |

EXAMPLE 4

Preparation of N,N-Dimethyl-α-phenyl-m-dioxane-5-methylamine hydrochloride 2-(α-Dimethylamino)benzyl-1,3-propanediol, 137 g. (0.66 mole), and 300 g. (10.0 mole) of paraformaldehyde were added to 1000 ml. of acetonitrile. Boron trifluoride etherate, 500 ml, 560 g. (3.96 mole), was added dropwise to the stirred reaction mixture, and the mixture was refluxed for 2 hours. The cooled reaction mixture was poured into a saturated solution of sodium bicarbonate and extracted with ether. The ether extract was washed with water, dried over anhydrous magnesium sulfate, and evaporated to an oily residue. The hydrochloride salt was prepared by treating an ethereal solution of the oil with gaseous hydrogen chloride. The yield was 97 g. of N,N-dimethyl-α-phenyl-m-dioxane-5-methylamine hydrochloride, mp about 172° C. after recrystallization from methanol-ethyl acetate.

Analysis: Calcd. for $C_{13}H_{19}NO_2HCl$: C, 60.58; H, 7.82; N, 5.43. Found: C, 60.78; H, 8.03; N, 5.40.

EXAMPLE 5

Alternate preparation of
N,N-dimethyl-α-phenyl-m-dioxane-5-methylamine hydrochloride A. 5-Benzoyl-m-dioxane.-

Sixty grams (0.5 mole) of acetophenone and 150 g. (5.0 mole) of paraformaldehyde were added to 500 ml. of acetonitrile. Boron trifluoride etherate, 213 g. (1.5 mole), was added dropwise to the stirred reaction mixture. The mixture reached reflux temperature by the time one-half of the boron trifluoride etherate had been added. The addition was completed and the reaction mixture was refluxed for 2 hours. The cooled reaction mixture was stirred into a mixture of ice, water and saturated sodium bidarbonate solution. The resultant melt was extracted with ether. The ether extract was washed with water, dried over anhydrous magnesium sulfate and evaporated in vacuo to an oil. The oil was distilled and the fraction bp 115°–120° C. (0.5 mm.) was collected to yield 40 g. of 5-benzoyl-m-dioxane which was characterized by NMR.

B. N,N-Dimethyl-α-phenyl-m-dioxane-5-methylamine hydrochloride.- Titanium tetrachloride, 2.75 ml., 4.75 g. (0.025 mole), in 50 ml. of benzene, was added dropwise under nitrogen to 9.5 g (0.05 mole) of 5-benzoyl-m-dioxane and 20 ml. of anhydrous dimethylamine in 200 ml. of benzene cooled in an ice bath with stirring. After coming to room temperature, the reaction mixture was refluxed for about 5 hours. The cooled reaction mixture was filtered and the filtrate was evaporated in vacuo to an oil. The oil was taken up in 200 ml. of ethanol and hydrogenated at 50 psi with 0.5 g. of 5 percent palladium-on-carbon for six hours. The catalyst was filtered and the filtrate was evaporated in vacuo to an oil whih was taken up in ether. The ether phase was extracted with dilute hydrochloric acid and washed with water. The aqueous wash and the acid extract were combined and basified with ammonium hydroxide. The basic solution was extracted with ether. The ether extract was washed with water, dried over anhydrous magnesium sulfate and evaporated in vacuo to yield 6 g. of oil. The oil was taken up in ether and treated with gaseous hydrogen chloride. The salt was collected and recrystallized from methanol-ethyl acetate to yield 0.3 g. of N,N-dimethyl-α-phenyl-m-dioxane-5-methylamine hydrochloride, mp about 172° C.

Analysis: Calc. for $C_{13}H_{19}NO_2$ HCl. C, 60.58; H, 7.82; N, 5.43. Found: C, 60.83; H, 7.90; N, 5.58.

EXAMPLE 6

Resolution of
dl-N,N-Dimethyl-α-phenyl-m-dioxane-5-methylamine

A. Preparation of dibenzoyl-l-tartaric acid salt.- dl-N,N-Dimethyl-α-phenyl-m-dioxane-5-methylamine, 1106.5 g. (5.0 mole), was dissolved in 4 liters of ethyl acetate. Dibenzoyl-l-tartaric acid monohydrate, 940.8 g. (2.5 mole), was dissolved in 4 liters of ethyl acetate by warming. The warm tartaric acid solution was added to the amine solution and immediately an oil formed. Methanol, 300 ml., was added to the mixture and crystallization of the oil was effected by warming on the steam bath. The crystallization was completed by standing overnight. The salt was collected and recrystallized from 5 l. of ethyl acetate with the minimum amount of methanol needed for solution. The crystalline salt was collected and the crystallization was again repeated to yield 548 g. of l-N,N-dimethyl-α-phenyl-m-dioxane-5-methylamine dibenzoyl-l-tartaric acid salt, mp about 132°–133° C., $[\alpha]_D^{25} + 61.40°$ (c=1, ethanol).

B. l-N,N-Dimethyl-dα-phenyl-m-dioxane-5-methylamine hydrochloride.- l-N,N-Dimethyl-α-phenyl-m-dioxane-5-methylamine dibenzoyl-l-tartaric acid salt, 543 g., was suspended in distilled water and basified with ammonium hydroxide. The basic mixture was extracted with ether. The ether extract was washed with water, dried over anhydrous magnesium sulfate and evaporated to a solid residue. The solid, 210 g., was taken up in ether and treated with gaseous hydrogen chloride. The salt was collected and recrystallized from methanol-ethyl acetate to yield 156 g. of l-N,N-dimethyl-α-phenyl-m-dioxane-5-methylamine hydrochloride, mp about 202°–203° C. $[\alpha]_{275}^{27°}$ - 92.6 (c=51.825 mg./5 ml., water)

Analysis: Calcd for $C_{13}H_{19}NO_2$ HCl. C, 60.58; H, 7.82; N, 5.43; Cl, 13.75. Found: C, 60.83; H, 7.58; N, 5.51; Cl, 13.67.

EXAMPLE 7

Preparation of
N,N-Dimethyl-α-(4-methylphenyl)-m-dioxane-5-methylamine maleate

A. Diethyl (4-methylbenzal)malonate.- Following the method of Example 1 one hundred grams (0.83 mole) of p-tolualdehyde, 133 g. (0.83 mole) of diethylmalonate and 5 ml. of piperidine, were reacted in benzene. The yield of diethyl (4-methylbenzal)malonate, bp 140° C. (0.7 mm), was 89 g.

Analysis: Calc. for $C_{15}H_{18}O_4$: C, 68.68; H, 6.92. Found: C, 68.94; H, 7.08.

B. Diethyl α-dimethylamino-(4-methylbenzyl)-malonate.- Following the method of Example 2 twenty grams of diethyl (4-methylbenzal)malonte and 100 ml. of anhydrous dimethylamine were reacted in ether to provide 22 g. of diethyl α-dimethylamino-4-methylbenzylmalonate as an oil.

C. 2-[α-Dimethylamino-(4-methylbenzyl)]-1,3-propanediol.- Diethyl α-dimethylamino-(4-methylbenzyl)malonate, 22 g. (0.77 mole), in 100 ml. of benzene, was added dropwise to a solution of 28 ml. (0.2 mole) of sodium bis(2-methoxyethoxy)aluminum hydride as a 70% solution in benzene, in 100 ml. of benzene cooled in an ice bath. After the addition, the reaction mixture was allowed to come to room temperature, and then it was refluxed for 2 hours. The cooled reaction mixture was decomposed with dilute sodium hydroxide solution. The phases were separated and the benzene layer was washed with water. The benzene phase was extracted with dilute hydrochloric acid and washed with water. Six grams of neutral oil was obtained from the benzene phase. The acidic aqueous extract was basified wit ammonium hydroxide and extracted with ether. The ether extract was washed with water, dried over anhydrous magnesium sulfate and was evaporated to a residual solid. The solid was recrystallized from ethyl acetate-hexane to yield 2.7 g. of 2-(α-dimethylamino-4-methylbenzyl)-1,3-propanediol, mp about 125°C.

Analysis: Calc. for $C_{13}H_{21}NO_2$: C, 69.92; H, 9.48; N, 6.27. Found: C, 70.08; H, 9.55; N, 6.05.

D. N,N-Dimethyl-α-(4-methylphenyl)-m-dioxane-5-methylamine maleate. Following the method of Example 4, 2-(α-dimethylamino-4-methylbenzyl)-1,3-propanediol, 2 g., and 10 g. of paraformaldehyde, in 50 ml. of acetonitrile, were treated with 3 ml. of boron trifluoride etherate. Extraction of the spent reaction mixture yielded 2.0 g. of oil. The maleate salt was prepared by treating the 2.0 g. of oil with 1 g. of maleic acid in ethyl acetate solution. Recrystallization of the salt from methanol-ethyl acetate yielded 1.5 g. of N,N-dimethyl-α-(4-methylphenyl)-m-dioxane-5-methylamine maleate, mp about 138°C.

Analysis: Calc. for $C_{14}H_{21}NO_2 \cdot C_4H_4O_4$: C, 61.52; H, 7.17; N, 3.99. Found: C, 61.60; H, 7.38; N, 3.80.

EXAMPLE 8

Preparation of N,N-Dimethyl-α-(3-pyridyl)-m-dioxane-5-methylamine dihydrochloride A. Diethyl (3-pyridyl)methylenemalonate.-

One hundred grams (0.935 mole) of 3-pyridinecarboxaldehyde, 150 g. (0.935 mole) of diethyl malonate and 5 ml. of piperidine were refluxed for 16 hours in 200 ml. of benzene with azeotropic distillation of 17 ml. of water. The cooled reaction mixture was poured into water and the benzene phase was separated. The benzene layer was washed successively with saturated sodium bicarbonate solution and water, dried over anhydrous magnesium sulfate and evaporated in vacuo. The oil residue was distilled to yield 180 g. of diethyl (3-pyridyl)methylene malonate, bp 143°C. (0.10 mm), which was characterized by NMR.

B. Diethyl α-dimethylamino-(3-pyridyl)methylmalonate.-

Following the method of Example 2, fifty grams of diethyl (3-pyridyl)methylenemalonate and 200 ml. of anhydrous dimethylamine were reacted in 200 ml. of ether to yield 56 g. of diethyl α-dimethylamino-(3-pyridyl)methylmalonate which was characterized by NMR.

C. 2-[α-Dimethylamino-(3-pyridyl)methyl]-1,3-propanediol.

Nineteen grams (0.5 mole) of lithium aluminum hydride was covered by 200 ml. of dry tetrahydrofuran (THF). Sixty nine grams (0.24 mole) of diethyl α-dimethylamino-(3-pyridyl)methylmalonate, dissolved in 300 ml. of dry THF, was added dropwise to the hydride slurry cooled in a icebath. The stirred reaction mixture was allowed to come to room temperature overnight. The mixture was decomposed by the addition of saturated sodium acetate solution and the volume was concentrated to 1/3 the original volume by evaporation in vacuo. The concentrated mixture was acidified with dilute hydrochloric acid and extracted with ether. The acidic aqueous phase was basified with dilute sodium hydroxide. The basic mixture was extracted with chloroform. The chloroform extract was washed with water, dried over anhydrous magnesium sulfate and evaporated to yield 40 g. of 2-[α-dimethylamino-(3-pyridyl)methyl]-1,3-propanediol which was characterized by NMR.

D. N,N-Dimethyl-α-(3-pyridyl)-m-dioxane-5-methylamine dihydrochloride.- Following the method of Example 4, seven grams of 2-[α-dimethylamino-(3-pyridyl)methyl]-1,3-propanediol, 30 g. of paraformaldehyde and 50 ml. of boron trifluoride etherate were reacted in 100 ml. of acetonitrile to yield 6 g. of the free base. The salt was prepared by treating an ethereal solution of the base with gaseous hydrogen chloride to yield 1.0 g. of N,N-dimethyl-α-(3-pyridyl)-m-dioxane-5-methylamine dihydrochloride, mp about 196° C., after recrystallization from methanol-ethyl acetate.

Analysis: Calc. for $C_{12}H_{18}N_2O_2 \cdot 2HCl$: C, 48.82; H, 6.83; N, 9.49. Found: C, 48.65; H, 6.79; N, 9.60.

EXAMPLE 9

Alternate preparation of N,N-dimethyl-α-(3-pyridyl)-m-dioxane-5-methylamine dihydrochloride 2-[α-Dimethylamino-(3-pyridyl)methyl]-1,3-propanediol, 10.5 g. (0.05 mole), 10 g. of trioxane, and 21 g. (0.11 mole) of p-toluenesulfonic acid were refluxed overnight in 200 ml. of chloroform in a flask fitted with a Soxhlet extractor containing 3A molecular sieve in the thimble. The cooled reaction mixture was washed twice with water. The aqueous solution was basified with ammonium hydroxide and extracted with chloroform. The chloroform extract was washed with water, dried over anhydrous magnesium sulfate and was evaporated to yield 6 g. of the free base. The salt was prepared to yield 1.0 g. of N,N-dimethyl-α-(3-pyridyl)-m-dioxane-5-methylamine dihydrochloride, mp about 195°C., after recrystallization from methanol-ethyl acetate.

EXAMPLE 10

Preparation of N,N,2-Trimethyl-α-phenyl-m-dioxane-5-methylamine 2-(α-Dimethylamino)benzyl-1,3-propanediol, 2.5 g. (0.012 mole), was dissolved in 25 ml. of acetonitrile. Water, 7.68 g. (0.48 mole), 10 ml. of acetaldehyde and 3.01 ml. (0.024 mole) of boron trifluoride etherate were added to the reaction mixture and the mixture was allowed to stir overnight. The reaction mixture was heated on the steam bath for 1 hour. The cooled mixture was poured into ammonium hydroxide and the basic mixture was extracted with ether. The ether extract was washed with water, dried over magnesium sulfate and evaporated to a solid residue. The solid was recrystallized from hexane to yield 0.44 g. of N,N,2-trimethyl-m-dioxane-5-methylamine, mp about 140°–143° C.

Analysis: Calc. for $C_{14}H_{21}NO_2$: C, 71.46; H, 9.00; N, 5.85. Found: C, 71.22; H, 8.92; N, 5.68.

EXAMPLES 11-13

The following compounds were prepared according to the method of Example 10 from 2-(α-dimethylamino)benzyl-1,3-propanediol and the appropriate aldehyde:

N,N-dimethyl-2-ethyl-α-phenyl-m-dioxane-5-methylamine, mp 95°–98° C.

Analysis: Calc. for $C_{15}H_{23}NO_2$: C, 72.25; H, 9.30; N, 5.62. Found: C, 72.49; H, 9.60; N, 5.69.

N,N-dimethyl-2-isopropyl-α-phenyl-m-dioxane-5-methylamine hydrochloride, mp 196°–199°C.

Analysis: Calc. for $C_{16}H_{25}NO_2 \cdot HCl$: C, 64.09; H, 8.74; N, 4.67. Found: C, 63.84; H, 8.99; N, 4.80.

N,N-dimethyl-α,2-diphenyl-m-dioxane-5-methylamine, mp, 105°–108° C.

Analysis: Calc. for $C_{19}H_{23}NO_2$: C, 76.74; H, 7.80, N, 4.71. Found: C, 76.91; H, 7.82; N, 4.45.

EXAMPLE 14

Preparation of N,N,4-Trimethyl-α-phenyl-m-dioxane-5-methylamine hydrochloride A. 5-Benzoyl-4-methyl-m-dioxane.- Phenylpropenyl ketone, 30 g. (0.2 mole), and 18 g. (0.20 mole) of strioxane, were refluxed in 300 ml. of chloroform. Boron trifluoride etherate, 20 ml., was added to the reaction mixture. Immediately an exothermic reaction occurred and heating was discontinued until the initial reaction had subsided. Subsequently, refluxing was resumed for about 15 minutes. The reaction mixture was poured onto a mixture of ice and saturated sodium bicarbonate solution. The resultant melt was extracted with ether. The ether extract was washed with water, dried over anhydrous magnesium sulfate, and evaporated to an oil. The oil was distilled and the fraction, bp, 110°–110° C. (0.50 mm.), was collected to yield 16 g. of 5-benzoyl-4-methyl-m-dioxane which was characterized by NMR.

B. N,N,4-Trimethyl-α-phenyl-m-dioxane-5-methylamine hydrochloride. To a stirred solution of 16 g. (0.08 mole) of 5-benzoyl-4-methyl-m-dioxane, and 40 ml. of anhydrous dimethylamine in 200 ml. of benzene cooled in an ice bath was added a solution of 7.6 g. (0.04 mole) of titanium tetrachloride in 50 ml. of benzene. The stirred solution was cooled at about 0° C. for 1 hour. The reaction mixture was allowed to come to room temperature overnight. The reaction mixture was diluted with ethanol and filtered to remove titanium dioxide. The filtrate was evaporated, the residual oil was taken up in 100 ml. of ethanol and hydrogenated at 60 psi with 0.5 g. of 5% palladium-on-carbon catalyst. After the catalyst was filtered and the filtrate evaporated, the residual oil was taken up in dilute hydrochloric acid. The acidic solution was extracted with ether and the extracts were discarded. The acidic solution was basified with ammonium hydroxide solution and the basic solution was extracted with ether. The ether extract was washed with water, dried over anhydrous magnesium sulfate and evaporated to yield 6 g. of oil. The oil was chromatographed on a silica gel column using 370 ml. of ethyl acetate-benzene gradient (1:4). One gram of N,N,4-trimethyl-α-phenyl-m-dioxane-5-methylamine was collected in the last 180 ml. of eluate. The salt was prepared by treating an ethereal solution of the free base with gaseous hydrogen chloride. The yield of N,N,4-trimethyl-α-phenyl-m-dioxane-5-methylamine hydrochloride, mp about 213° C., was 0.7 g. after recrystallization from methanolethyl acetate.

Analysis: Calc. for $C_{14}H_{21}NO_2$ HCl: C, 61.87; H, 8.16; N, 5.15. Found: C, 61.63; H, 8.13; N, 5.25.

EXAMPLE 15

Preparation of N,N,5-Trimethyl-α-phenyl-m-dioxane-5-methylamine hydrochloride A. 5-Benzoyl-5-methyl-m-dioxane.- Paraformaldehyde, 9 g. (0.30 mole), was dissolved in 100 ml. of acetonitrile by warming and 13.4 g. (0.10 mole) of propiophenone was added to the mixture. The mixture was cooled in an ice bath and 15 g. (0.10 mole) of boron trifluoride etherate was added dropwise at about 0°C. The solution became turbid. The turbid mixture was clarified by boiling for about 15 minutes on the steam bath. The boiled solution was stirred into a mixture of ice and saturated sodium bicarbonate solution. The amber layer which separated from the aqueous melt was extracted with ether. The ether extract was washed with water, dried over anhydrous magnesium sulfate, and evaporated in vacuo to give 17 g. of oil. The oil was distilled and the fraction, bp 120°–130° C. (0.40 mm.), was collected. The redistilled fraction, bp 118°–122° C. (0.40 mm.), crystallized. The yield of 5-benzoyl-5-methyl-m-dioxane, mp about 84° C., was 2.1 g. after recrystallization from acetone-hexane.

Analysis: Calc. for $C_{12}H_{14}O_3$: C, 69.88; H, 6.84. Found: C, 70.08; H, 6.62.

B. 5-Benzoyl-5-methyl-m-dioxane oxime.- Two grams of 5-Benzoyl-5-methyl-m-dioxane and 2 g. of hydroxylamine hydrochloride in 10 ml. of ethanol and 10 ml. of pyridine were refluxed for 3 hours. The mixture was evaporated to dryness in vacuo and the residue was treated with 10 ml. of water. The oxime was collected and recrystallized from aqueous ethanol to yield 1.5 g. of 5-benzoyl-5-methyl-m-dioxane oxime, mp about 144° C.

Analysis: Calc. for $C_{12}H_{15}NO_3$: C, 65.14; H, 6.83. Found: C, 65.36; H, 6.93.

C. 5-Methyl-α-phenyl-m-dioxane-5-methylamine.- Lithium aluminum hydride, 1.37 g. (0.036 mole), was covered with 100 ml. of dry tetrahydrofuran (THF). 5-Benzoyl-5-methyl-m-dioxane oxime, 4.0 g. (0.018 mole), was dissolved in 50 ml. of THF and added dropwise to the stirred hydride suspension. The stirred mixture was refluxed for 1 hour and then cooled. The mixture was decomposed with saturated ammonium chloride solution and the aqueous phase was decanted. The residue was treated twice with ether. The ether was evaporated and the residue was again taken up in ether. The hydrochloride salt was prepared by treatment of the ethereal solution with gaseous hydrogen chloride. The salt was dissolved in water and the aqueous phase was extracted with ether. The ether extract was washed with water. The aqueous phase and the water washes were combined and basified with ammonium hydroxide. The basic solution was extracted with ether. The ether extract was washed with water, dried over anhydrous magnesium sulfate, and treated with gaseous hydrogen chloride to provide the salt of the product. The yield of 5-methyl-α-phenyl-m-dioxane-5-methylamine hydrochloride, mp about 235° C. with decomposition, was 2.26 g. after recrystallization from methanolethyl acetate.

Analysis: Calc. for $C_{12}H_{17}NO_2$ HCl: C, 59.13; H, 7.44. Found: C, 59.07; H, 7.56.

(D) N,N,5-Trimethyl-α-phenyl-m-dioxane-5-methylamine hydrochloride.- Five grams of 5-methyl-α-phenyl-m-dioxane-5-methylamine hydrochloride was converted to the free base by dissolving the salt in water, basifying with ammonium hydroxide and extracting the basic solution with ether. The ether extract was washed with water, dried over anhydrous magnesium sulfate and evaporated to provide the free base as an oil. The oil was taken up in 25 ml. of cold 90% formic acid. Twenty-five milliliters of 38% aqueous formaldehyde was added to the cold reaction mixture and the mixture was heated on the steam bath for about 12 hours. The reaction mixture was poured onto a mixture of ice and water and basified with dilute sodium hydroxide. The basic aqueous solution was extracted with ether. The ether extract was washed with water, dried over anhydrous magnesium sulfate, and evaporated to an oil. The salt was prepared by treating an ethereal solution of the oil with gaseous hydrogen chloride. The yield of N,N,5-trimethyl-α-phenyl-m-dioxane-5-methylamine hydrochloride, mp about 195° C., was 3.0 g. after recrystallization from methanol-ethyl acetate.

Analysis: Calc. for $C_{14}H_{21}NO_2$ HCl: C, 61.87; H, 8.16; N, 5.15. Found: C, 61.74; H, 8.41; N, 4.98.

EXAMPLE 16

Preparation of N-Allyl-N-methyl-α-phenyl-m-dioxane-5-methylamine hydrochloride

A.  2-(α-N-Methylbenzylamino)benzyl-1,3-propanediol.-Two hundred grams (0.808 mole) of diethyl benzalmalonate and 89 g. (0.808 mole) of N-methylbenzylamine were allowed to stand overnight at room temperature. The resultant crude diethyl α-(N-methylbenzylamino)benzylmalonate was added dropwise to 560 ml. (2.0 mole) of sodium bis(2-methoxyethoxy)aluminum hydride as a 70% solution in benzene, in dry benzene and stirred overnight. The reaction mixture was poured into cold dilute sodium hydroxide solution. The basic solution was extracted with ether. The ether extract was washed with water, dried over anhydrous magnesium sulfate and evaporated to a residual oil. The yield was 233 g. of 2-(α-N-methylbenzylamino)benzyl-1,3-propanediol which was characterized by NMR.

B.  N-Benzyl-N-methyl-α-phenyl-m-dioxane-5-methylamine.- Following the method of Example 4, one hundred and twenty grams 2-(α-N-methylbenzylamino)benzyl-1,3-propanediol, 100 g. of paraformaldehyde and 200 ml. of boron trifluoride etherate were refluxed overnight in 500 ml. of acetonitrile. The reaction mixture was poured into ammonium hydroxide solution, and subsequent isolation provided 84 g. of free base as an oil. The salt was prepared to yield 25 g. of N-benzyl-N-methyl-α-phenyl-m-dioxane-5-methylamine hydrochloride, mp about 193°–195° C., which was characterized by NMR.

C.  N-Methyl-α-phenyl-m-dioxane-5-methylamine hydrochloride.- Eighteen grams of N-benzyl-N-methyl-α-phenyl-m-dioxane-5-methylamine was hydrogenated at 60 psi in 80 ml. of ethanol with 0.9 g. of 5% palladium-on-carbon catalyst at 35° C. for 1¼ hours. The catalyst was filtered and the filtrate was evaporated to a residual oil. The oil was taken up in ether and the ethereal solution was treated with gaseous hydrogen chloride to yield 3.7 g. of N-methyl-α-phenyl-m-dioxane-5-methylamine hydrochloride, mp about 155°–157° C., after crystallization from methanol-ethyl acetate.

Analysis: Calc. for $C_{12}H_{17}NO_2$ HCl: C, 59.13; H, 7.44; N, 5.75; Cl, 14.55. Found: C, 58.91; H, 7.43; N, 5.82; Cl, 14.82.

D. Alternate preparation of N-methyl-α-phenyl-m-dioxane-5-methylamine hydrochloride.- N,N-Dimethyl-α-phenyl-m-dioxane-5-methylamine, 5.5 g (0.025 mole), and 4.5 g (0.025mole) of diethyl azodicarboxylate were allowed to stand overnight in 100 ml. of benzene. The reaction mixture was evaporated in vacuo and 50 ml. of saturated ammonium chloride was added to the residue. Enough ethanol was added to obtain a homogeneous solution and the mixture was heated on the steam bath for 5 hours. The cooled mixture was extracted with ether. The aqueous phase was basified with ammonium hydroxide and extracted with ether. The ether extract was washed with water, dried over anhydrous magnesium sulfate and evaporated in vacuo to an oil. The oil was chromatographed over silica gel using ethyl acetatebenzene (1:4) as eluant. About 3 g. of starting material was eluted first. Continued elution with ethyl acetate gave 2 g. of oil. The salt was prepared by treating an ethereal solution of the oil with gaseous hydrogen chloride to yield 1.1 g of N-methyl-α-phenyl-m-dioxane-5-methylamine hydrochloride, mp about 183°–4° C., after recrystallization from methanol-ethyl acetate.

Analysis: Calcd for $C_{12}H_{17}NO_2$ HCl: C, 59.13; H, 7.44; N, 5.75. Found: C, 58.90; H, 7.51; N, 5.64.

E. N-Allyl-N-methyl-α-phenyl-m-dioxane-5-methylamine hydrochloride.- N-Methyl-α-phenyl-m-dioxane-5-methylamine, 2.1 g. (8.65 millimole), 1.05 g. (8.65 millimole) of allyl bromide and 0.59 g. (4.32 millimole) of potassium carbonate were refluxed in 100 ml. of acetone for several hours. The mixture was evaporated and the residue was taken up in water. The aqueous phase was extracted with ether. The ether extract was washed with water, dried over magnesium sulfate and evaporated to an oil. The product was separated from starting material by silica gel chromatography using ethyl acetate as the eluant. The salt was prepared by reating an ethereal solution of the free base with gaseous hydrogen chloride to yield 1.2 g. of N-allyl-N-methyl-α-phenyl-m-dioxane-5-methylamine hydrochloride, mp about 193°–195° C.

Analysis Calc. for $C_{15}H_{21}NO_2$ HCl: C, 63.48; H, 7.81 N, 4.94. Found: C, 63.26; H, 7.84; N, 4.88.

I claim:

1. A compound of the formula

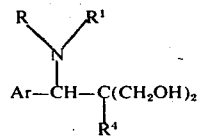

wherein
R and $R^1$ are $C_1$-$C_4$ alkyl, $C_2$-$C_4$ alkenyl or benzyl; or when taken together with the nitrogen atom to which they are attached are aziridino, pyrrolidino or piperidino;
$R^4$ is hydrogen or methyl; and
Ar is phenyl, halophenyl, hydroxyphenyl, methoxyphenyl, methylphenyl, trifluoromethylphenyl or 3-pyridyl.

2. The compound of claim 1 where R and $R^1$ are $C_1$-$C_4$ alkyl.

3. The compound of claim 2 which is 2-α-dimethylaminobenzyl-1,3-propanediol.

4. The compound of claim 2 which is 2-[α-dimethylamino(3-pyridyl)methyl]-1,3,-propanediol.

* * * * *